United States Patent [19]

Reichelt

[11] Patent Number: 4,744,240

[45] Date of Patent: May 17, 1988

[54] METHOD FOR DETERMINING THE BUBBLE POINT OR THE LARGEST PORE OF MEMBRANES OR OF FILTER MATERIALS

[75] Inventor: Gert Reichelt, Obernburg, Fed. Rep. of Germany

[73] Assignee: Akzo NV, Arnhem, Netherlands

[21] Appl. No.: 53,485

[22] Filed: May 26, 1987

[30] Foreign Application Priority Data

May 27, 1986 [DE] Fed. Rep. of Germany ....... 3617724

[51] Int. Cl.$^4$ ............................................. G01N 15/08
[52] U.S. Cl. ........................................................ 73/38
[58] Field of Search ............................. 73/38, 64.3, 19

[56] References Cited

U.S. PATENT DOCUMENTS

| 4,449,392 | 5/1984 | Huschke | 73/38 |
| 4,614,109 | 9/1986 | Hofmann | 73/38 |

FOREIGN PATENT DOCUMENTS

| 8212094 | 8/1982 | Fed. Rep. of Germany. | |
| 3306647 | 8/1984 | Fed. Rep. of Germany | 73/38 |
| 3312729 | 10/1984 | Fed. Rep. of Germany | 73/38 |
| 224936 | 7/1985 | German Democratic Rep. | 73/38 |
| 2140163 | 11/1984 | United Kingdom | 73/38 |

Primary Examiner—Stewart J. Levy
Assistant Examiner—Hezron E. Williams
Attorney, Agent, or Firm—Parkhurst & Oliff

[57] ABSTRACT

When determining the bubble point or the largest pore of a membrane or of a filter material, the membrane or the filter material is placed in a container, with the membrane or the filter material thus dividing this container into two compartments. Then, the first compartment is filled with gas, and the second compartment and the pores of the membrane (or the filter material) are filled with a wetting liquid. The pressure in the gas compartment is raised at least until the gas displaces the liquid from the largest pore. The bubble point is defined by means of the gas-compartment pressure then prevailing, or the cross-sectional dimension of the largest pore can be calculated. According to the invention, the gas-compartment pressure corresponding to the bubble point is determined by measuring a sudden increase in the sound intensity in the liquid compartment. The measurement of the sound intensity is preferably carried out in the ultrasonic range.

3 Claims, 2 Drawing Sheets

METHOD FOR DETERMINING THE BUBBLE POINT OR THE LARGEST PORE OF MEMBRANES OR OF FILTER MATERIALS

TECHNICAL FIELD

The present invention relates to a method for determining the bubble point or the largest pore of membranes or filter materials. The membranes or filter materials are placed in a container and divide it into a first and a second chamber. The first chamber is filled with gas and the second chamber and the pores of the membrane or filter material are filled with a liquid that wets the membrane or filter material. The pressure in the first chamber is then increased over time from the normal pressure at least until a pressure in the gas compartment is established at which the gas displaces the liquid from the largest pore of the membrane or filter material. The bubble point is defined by means of the gas-compartment pressure then prevailing, or the cross-sectional dimension of the largest pore can be calculated.

BACKGROUND OF THE INVENTION

Such methods are taught, for example, by West German Utility Model No. 8,212,094. In the prior art process, the pressure in the gas compartment at which the gas displaces the liquid from the largest pore of the membrane or filter material is determined by measuring the differential pressure between the liquid compartment and the surroundings, the change of this differential pressure over time being used as a measure for the rate of flow of the gas through the pores. For relatively large pores, the flow rate can also be measured directly (ASTM F 316-70), or the rising of bubbles can be observed visually (ASTM E 128-61).

However, as explained in West German Pat. No. 3,306,647, in these prior art methods it has been observed that with an increase in size of the membrane area to be examined and of the pore diameters present in the membrane, a certain gas flow rate can be noted even before the pressure determined by the bubble point has been reached, so that the measured result with respect to the bubble point and the largest pore is distorted. For example, this flow rate can be caused by a diffusion flow, which is causally related to the solubility—proportional to the partial pressure—of gases in liquids and the resulting concentration gradients of the gas molecules in the pores of the membrane. Although, according to the method described in West German Pat. No. 3,306,647, this undesired phenomenon is prevented, the use of the method described therein is very time-consuming, so that only with a large staff is it possible to examine the number of membranes or of membrane modules necessary for production control.

SUMMARY OF THE INVENTION

An object of the present invention is to provide a very simple, yet reliable, method of the type mentioned above, with which, regardless of the membrane area or filter-material area to be examined, and regardless of the pore size, one can determine the bubble point and the largest pore diameter with sufficient accuracy. A method is also especially to be provided with which the bubble point and the largest pore diameter can be determined for whole modules, even membranes or filter materials which have already been embedded in their casings.

These and other objects are achieved by determining, during the increase of the pressure in the gas compartment over time, the sound intensity in the liquid compartment and the pressure in the gas compartment at which a sudden increase of the sound intensity can be detected.

BRIEF DESCRIPTION OF THE DRAWINGS

The invention will be explained in greater detail by reference to the following Figures, in which.

DETAILED DESCRIPTION OF PREFERRED EMBODIMENTS OF THE INVENTION

Figure 1:
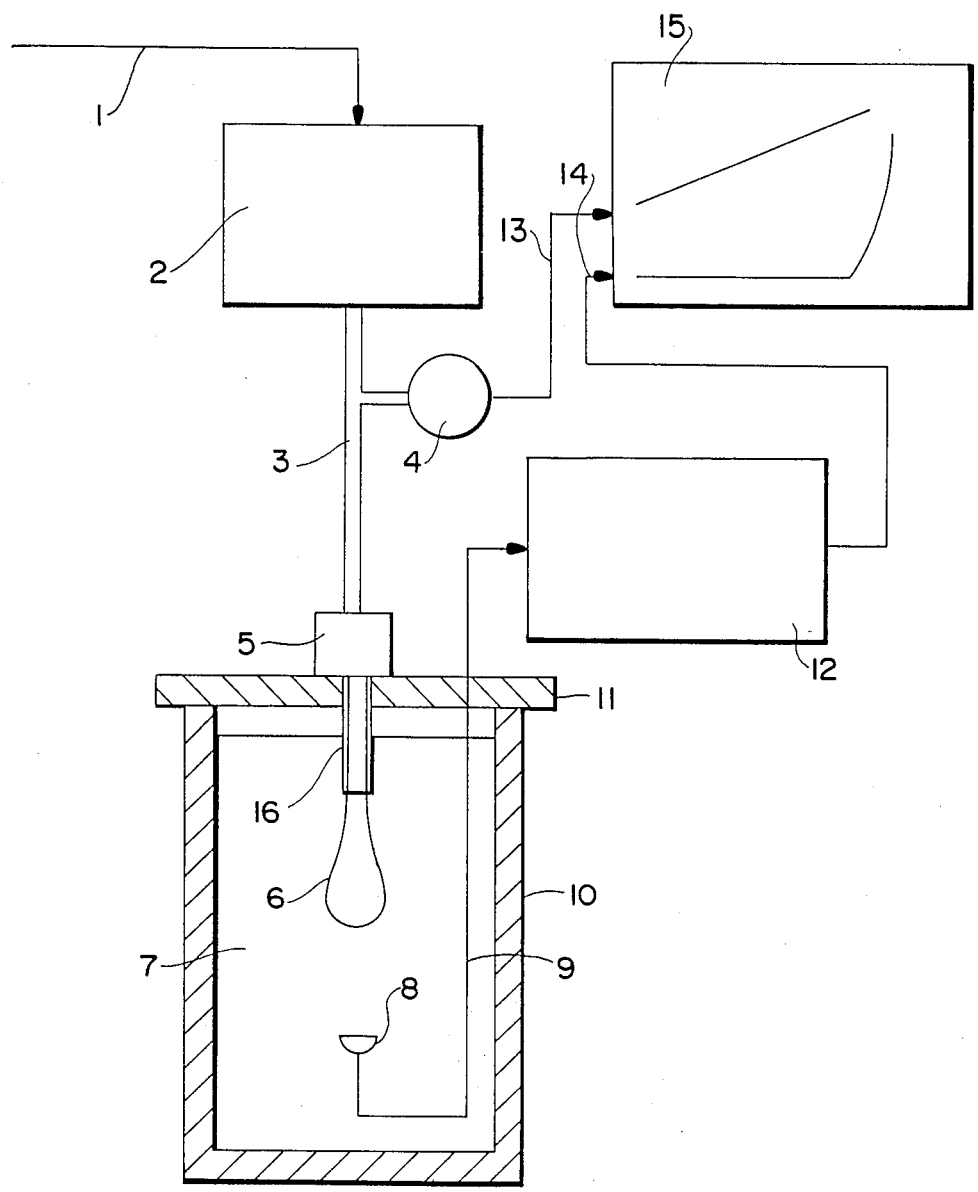
FIG. 1 schematicallly shows an arrangement for conducting the method of the invention.

As a rule, a diagram is prepared in which the sound intensity is plotted against the pressure in the gas compartment. Here, it is observed that the sound intensity (noise level) is at first of uniform value when the pressure in the gas compartment is low. It has now been determined that the sound intensity increases suddenly when the pressure corresponding to the bubble point is reached. This sudden increase can occur continuously or discontinuously, depending on the pore distribution. According to the invention, it has been determined that the gas-compartment pressure corresponding to the bubble point is reached whenever the sound intensity increases suddenly.

If the membranes or filter materials are examined in a testing device as, for example, described in West German Utility Model No. 8,212,094, a usually watertight microphone is now installed in the liquid compartment to substitute for the differential-pressure measurement described therein, and the signals of this microphone are appropriately amplified before they are recorded.

However, when carrying out the method of the invention, which is very simple and rapid to perform, the following points should be paid attention to:

Since when carrying out the bubble point measurement, gas bubbles may usually develop as a result of the gas contained in each liquid, the microphone must not be placed in an area in which these gas bubbles can rise.

The measuring vessel must be appropriately shielded from external interference (impact sound, conversations, etc.). The external interferences can also be effectively reduced by measuring the sound intensity in the ultrasonic range, i.e., at frequencies above 20 kHz. Sound-absorbing insulation around the measuring vessel is advisable.

The measuring vessel must be made of a material with which the losses that arise when sound is reflected at the vessel wall can be minimized. Glass or metal has proved most effective as the material if the sound reflected at the vessel wall can be kept very small. Glass or metal has proved best as material for the measuring vessel.

In order further to reduce the slight influence of the measuring-vessel wall, the distance between opposite walls ought to be at least 10 cm.

Care is to be taken to ensure that the membranes or filter materials are wetted thoroughly. For large membrane areas of membranes or filter materials, it has proved advantageous first to evacuate, then slowly to flood the same. In this case, before filling the pores with the wetting liquid, they are evacuated by application of a reduced pressure.

If the membranes or filter materials ar wetted poorly, air inclusions may occur. As a result, a relatively high background level is produced when carrying out the process of the invention.

If membranes or filter materials which are already embedded in a fixed casing are tested, the process of the invention can be carried out by submerging the membrane in the casing in a liquid, for example water, the microphone now being placed in this liquid. This setup can be chosen whenever the sound or ultrasound can penetrate the casing wall. In this way, an effective and simple production control for mass-transfer modules or for membranes already embedded in a casing is possible. It has been found that it is possible, by using the method of the invention, to measure pores whose area is 1000 times larger than the area of the specimens which can be measured with the necessary accuracy by means of the method taught by West German Utility Model No. 8,212,094.

FIG. 1 is a schematic representation of a setup for performing the method of the invention. Specimen 6, which in the example shown represents a hollow-fiber membrane, is embedded in a mount 16. Mount 16, as well as the free ends of the hollow-fiber membrane 6, terminate in a compartment 5. In the embodiment of FIG. 1, compartment 5 and the internal cavity of the hollow-fiber membrane form the gas compartment, which is connected via line 3 to a pressure control 2, which delivers the gas, e.g. nitrogen, via line 1, with the required pressure that increases with time. Coupled to line 3 is a precision pressure-measuring instrument 4, whose output signals are transmitted via line 13 to a Y-t recorder 15, which records the pressure signal against time.

Figure 2:
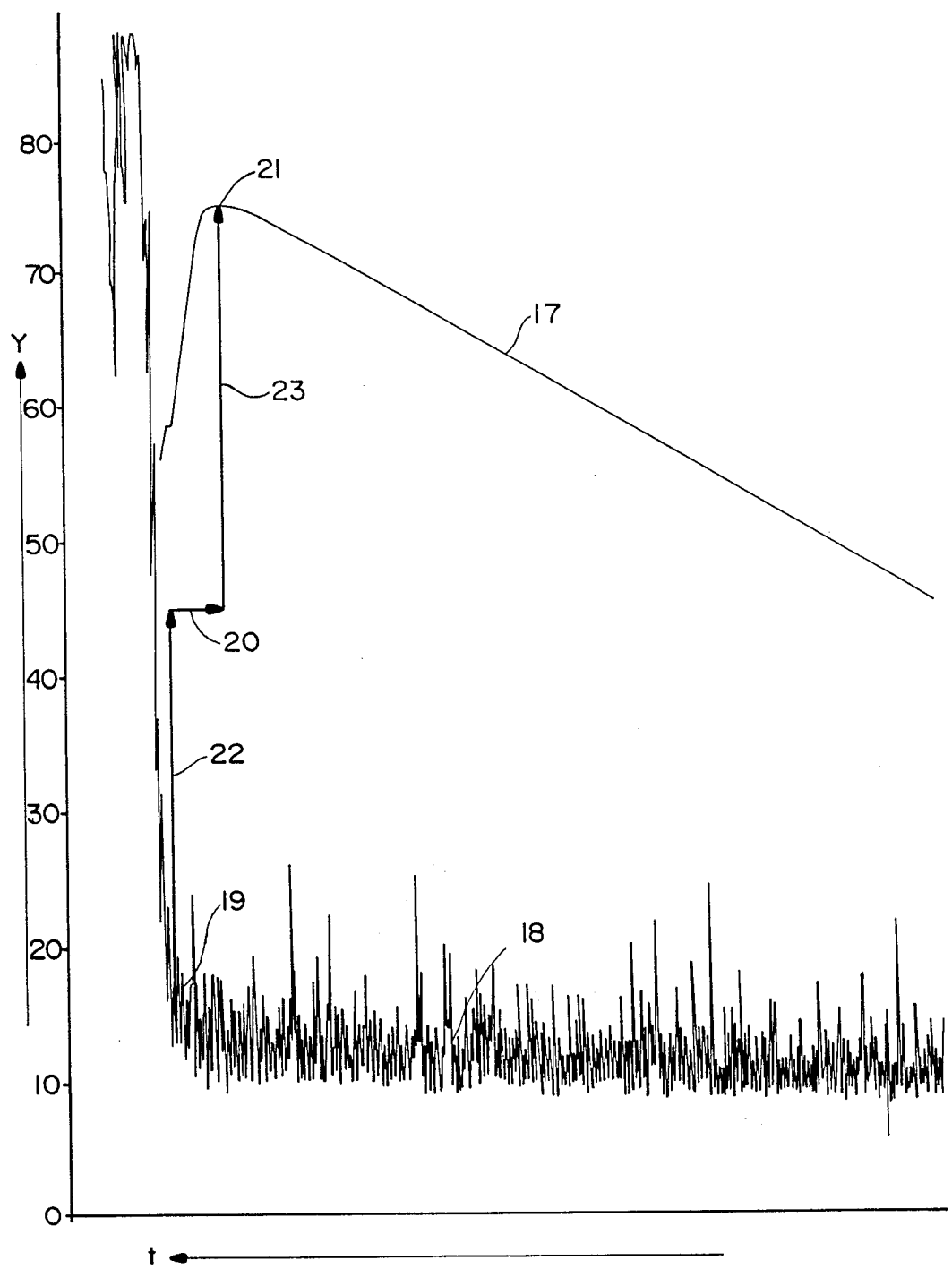
FIG. 2 shows a diagram prepared during conduct of the method of the invention.

Specimen 6 is submerged in liquid 7, which is filled into a vessel. The vessel is sheathed with sound insulation 10. At the same time, the vessel is closed at the top with sound insulation 11 as the cover. Beneath specimen 6 is placed, e.g., a watertight, piezoelectric quartz sensor microphone 8, whose signals are delivered via line 9 to a processor 12. In processor 12, the signals arriving from microphone 8 are filtered with respect to frequency (for example, in order to take advantage of the amplification resulting from the natural frequency of the microphone used), electrically amplified and rectified. Filtering is also necessary to eliminate noises caused by any turbulence in the measuring liquid. The amplified and filtered signals are also fed via line 14 to Y-t recorder 15, which, in parallel with the pressure signal, also records the signal of the sound intensity against time. FIG. 2 shows how such a diagram may be constructed.

As apparent from FIG. 2, in the printout of the Y-t recorder, the time is plotted in the direction of arrow t and the pressure in the gas compartment, as well as the sound intensity, is plotted in the direction of arrow Y.

Whereas the curve of the pressure in the gas compartment 17 rises, the curve of the average sound intensity 18 moves along a straight line which, however, rises suddenly at point 19. The pressure 21 corresponding to the bubble point is reached at this point 19 in terms of the pressure in the gas compartment. The coordination is shown by means of arrows 22, 20 and 23, the device-specific internal time shift between the two curves 17 and 18 being eliminated by means of rectifying arrow 20. The line of pressure curve 17 falling after point 21 is therefore due to the fact the pressure control 2 was turned off by the increase of the sound intensity at point 19.

The method of the invention is particularly cost-effective if membrane or filter means of more than 0.1 m² are to be tested. For membrane or filter areas of 2.4 or 8 m², bubble point and largest pore diameter can be readily measured. The maximum pore diameter $d_{max}$ can be calculated from the pressure in the gas compartment $P_B$ corresponding to the bubble point by means of the formula $$d_{max} = \sigma_B/P_B$$

in which $\sigma_B$ is a constant, which is essentially peculiar to the wetting liquid. The values for $\sigma_B$ at 25° C. are, for example, 0.611 micrometer.bar for isopropanol and 2.07 micrometer.bar for H₂O.

What is claimed is:

1. A method for determining the bubble point or the largest pore of a membrane or filter material, comprising:
   placing said membrane or filter material in a container in such a way as to divide the container into a first compartment and a second compartment;
   filling the first compartment with a gas and filling the second compartment and pores of the membrane or filter material with a liquid which wets the membrane or filter material;
   raising the gas pressure in the first compartment over time at least until a pressure in the first compartment is established at which the gas displaces the liquid from the largest pore of the membrane or filter material;
   measuring sound intensity in the second compartment while raising said pressure; and
   determining a pressure in said first compartment at which a sudden increase of the sound intensity can be detected.

2. The method according to claim 1, wherein the measurement of the sound intensity is conducted in an ultrasonic range.

3. The process according to claim 1, wherein the pores are evacuated by application of a reduced pressure before filling of the pores with the wetting liquid.

* * * * *